United States Patent [19]

Sirén

[11] Patent Number: 4,735,936

[45] Date of Patent: Apr. 5, 1988

[54] PHARMACEUTICAL COMPOSITION CONTAINING INOSITOL TRIPHOSPHATE

[76] Inventor: Matti Sirén, Casa Camboni, Via al Crespo, CH-6596 Gordola, Switzerland

[21] Appl. No.: 788,801

[22] Filed: Oct. 18, 1985

[30] Foreign Application Priority Data

Oct. 23, 1984 [SE] Sweden ................................ 8405295

[51] Int. Cl.$^4$ ............................................. A61K 31/66
[52] U.S. Cl. .................................... 514/103; 514/970;
252/400.2; 558/155
[58] Field of Search ................ 514/103, 970; 558/155;
252/400.2

[56] References Cited

U.S. PATENT DOCUMENTS 2,723,938 11/1955 Buckwalter et al. ................ 514/199
3,591,665 7/1971 Kimura et al. ................ 252/400.2 X
4,473,563 9/1984 Nicolau et al. ..................... 424/224

OTHER PUBLICATIONS

Chemical Abstract, vol. 33, Abstract No. 7351 (1939).
Nature, vol. 306, 67–69 (Nov. 1983).
Biochemical & Biophysical Res. Comm., vol. 120, No. 2, 481–485 (Apr. 30, 1984).
Tomlinson et al., Biochemistry, vol. 1, No. 1, pp. 166–171 (Jan. 1962).
Kerr et al., Archives of Biochemistry and Biophysics, vol. 96, pp. 347–353 (1962).

Primary Examiner—Lionel M. Shapiro
Attorney, Agent, or Firm—Scully, Scott Murphy & Presser

[57] ABSTRACT

A pharmaceutical composition containing as a pharmaceutically active ingredient at least one isomer of inositol triphosphate ($IP_3$) in an amount sufficient to reduce the negative effect of cadmium or aluminum in the body or inhibit or reduce the formation of free radicals in the body.

22 Claims, No Drawings

PHARMACEUTICAL COMPOSITION CONTAINING INOSITOL TRIPHOSPHATE

FIELD OF INVENTION

The present invention relates to the treatment and alleviation of conditions caused or aggravated by the presence of cadmium or aluminium or free radicals in the body, and more particularly to a pharmaceutical composition containing at least one isomer of inositol triphosphate ($IP_3$) for such treatment.

Methods of producing $IP_3$ and its isomers are disclosed in applicant's copending patent application Ser. No. 788,829 filed on the same day as this application and having the title "Inositol triphosphate" (applicant's case No. 355 b).

BACKGROUND OF THE INVENTION

Even as early as the year 1900, different researchers had reported the finding of the organic phosphate compound phytic acid, i.e., 1,2,3,4,5,6-hexakis (dihydrogenphosphate) myo-inositol (also sometimes called inositolhexaphosphoric acid) in plants. The content of phytic acid in different plants varies considerably. The content in grain is usually approximately 0.5-2%, with certain exceptions. Polished rice has a level of only 0.1% while wild rice contains as much 2.2% phytic acid. Beans contain about 0.4-2%, oil plants approximately 2-5% and pollen 0.3-2% The content of phytic acid in the plant varies during the growth period. The content is also influenced by, among other things, the climate.

In the literature there are reports on the presence of inositol pentaphosphate ($IP_5$) and inositol tetraphosphate ($IP_4$) in a few plants. It is further known that phosphate derivates lower than $IP_6$ are formed at germination of grain. For instance the final products at the germination are inositol and phosphate. The use of $IP_6$ has been described in several scientific publications. The majority of the authors of these articles have observed several negative effects on humans and animals when consuming $IP_6$ or substances containing $IP_6$. Feeding dogs with too high an amount of $IP_6$ gives rise for example to rachitis. In humans lack of zinc and as a consequence thereof slower growth of childern has been observed. Anemia has been observed mainly in women. Because of the above mentioned negative effects on the mineral balance in humans and animals, attempts have so far been made to reduce the intake of $IP_6$ and its derivatives to a minimum.

From C.A. Vol. 33 (1939), Abstr. No. 7351, No. 3/4 the use of phosphates including inositol phosphates as an anti-rachitic diet has been reported. No reference is made to specific inositol phosphates and nothing has been said in regard to complexing of metals.

U.S. Pat. No. 4,473,563 discloses the extracorporal treatment of erythrocytes to incorporate therein inositol phosphates to improve the oxygen supply. Then erythrocytes are separated from drawn blood which has been pumped out of the body for that purpose. After complicated treatment of erythrocytes the latter are re-introduced into the blood. There is no disclosure of administering inositol phosphates directly to the body. Moreover, nothing has been said in regard to reduction of the negative effect of cadmium in the body or the inhibition of the formation of free radicals in the body by a specially selected inositol phosphate.

In U.S. Pat. No. 2,723,938 the use of inositol phosphates is disclosed for stabilizing dispersions of acqueous suspension of penicillin. This insures that brief simple manual shaking will restore a state of complete and uniform dispersion of the penicillin after prolonged storage.

Cadmium has been found to be detrimental to human health. While this metal in general is present in a low level in our environment, the amount of cadmium we are exposed to depends on several factors. Cadmium occurence as well as its availability in the ground varies amoung different areas, with a relatively high uptake in plants growing in areas with relatively low pH value. By industrial activity, mainly handling of metals, cadmium can be released into the air, ground and water. Cadmium in soil is absorbed by plants and thus can come into the diet of human beings and animals. The most important routes of exposure to cadmium are via smoking, food and, to a certain extent, drinking water.

Cadmium is mainly absorbed in the intestine and through the lungs, although only a small part of the cadmium in the diet is absorbed. The average cadmium intake via food is estimated to be approximately 50 $\mu$g per day in most countries, but the variation is large among different geographic areas and among individuals. Data from smokers show that as much as 50% of the inhaled cadmium can be absorbed. Several investigations show twice as high blood- and organ-levels of cadmium in smokers compared to non-smokers. The excretion of cadmium from the human body is slow and a half-life of 10–30 years has been reported. This means that cadmium is accmulated in the body. The main part, 80–90% of the accumulated cadmium, is bound to a protein, metallothionein, mainly in the liver and kidneys. The formation of metallothionein is induced by metals, mainly zinc and cadmium. The binding of cadmium to metallothionein is very strong and results in a detoxification of cadmium. The remaining cadmium is in the body, i.e. that not bound to metallothioneins, is distributed among the other organs of the body with relatively high levels in the intestine, lungs (especially of smokers), the circulatory system (heart, artery walls, spleen) and glands like the pancreas and prostate.

Among the negative effects, it is known that cadmium an affect the elastin/elastase system of the body. It is also known that cadmium can affect several different enzymes in the body, examples of which are $Na^+$, $K^+$ ($Mg^{2+}$)-ATP-ase and $Ca^{2+}$, $Mg^{2+}$-ATP-ase, which are important in ion transport systems. Further examples are cytochrome-P450-enzymes which hydrolyse steroids, fatty acids, aromatic compounds and toxic compounds. Other important enzymes, which are inhibited by cadmium, are glutathion-peroxidase and superoxiddismutase, which protect against occurence of peroxidation. Zinc dependent enzymes, such as leucine-aminopeptidase, are also inhibited by cadmium.

Results from a large number of animal experiments obtained over many years show negative effects even at very low levels of cadmium. This would mean that a large proportion of the population is negatively affected, and this is above all valid for smokers. Epidemiological research shows a connection between the presence of cancer, high blood pressure and cardiovascular diseases (for instance, arteriosclerosis, heart infarction, sudden cardiac death) and the occurence of cadmium in the environment. Exposure to cadmium also seems to be a factor in increasing the risk of age diabetes.

There are also investigations showing that cadmium can have negative effects on the kidneys, lungs (fibrosis, emphysema, cancer), blood vessel walls (fat deposition, arteriosclerosis, vessel wall contraction, elasticity, damage to endothelium), prostacycline production, prostate, heart (conduction system, force of contraction), placenta, testicles and central nerve system. Cadmium can also induce the formation of free radicals and thereby cause lipid peroxidation, which can be important in the origin of other diseases like rheumatism. Allergies and bronchitis can also be connected with cadmium exposure. Knowledge of the negative influence of cadmium on humans and animals has increased considerably over the lase decades.

In spite of a very intensive research effort for many years seeking to prevent the above mentioned negative effects of cadmium and/or to prevent or alleviate the above mentioned problems created by cadmium, which in many cases involve very serious diseases, no good remedy without side effects has until now been found.

Aluminum has recently been recognized as a health hazard. In dialysis patients, aluminium causes dementia and osteomalicia.

It is suspected that aluminum may cause many abnormalities, such as Alzheimer's disease in humans. There are also investigations showing that aluminum can cause several diseases in animals. Aluminum can also increase lipid peroxidation in biological membranes, probably by destabilizing membrane structure. As for cadmium, no good remedy for Al-related diseases, without side effects has ntil now been found.

SUMMARY OF THE INVENTION

According to the present invention it has quite unexpectedly been found possible to solve the above mentioned negative effects of cadmium, aluminum and free radicals on humans and animals and thus also to prevent or alleviate the connected diseases. Thus, a pharmaceutical composition containing as a pharmaceutically active ingredient at least one isomer of inositol triphosphate ($IP_3$), preferably in salt form, has been brought about. The composition according to the invention is mainly intended to prevent or alleviate conditions created, induced or furthered by cadmium and aluminum intake, and to prevent or alleviate cadmium and aluminum related diseases. In addition, the composition is also intended for prevention or alleviation of diseases related to the presence of free radicals in the body.

DETAILED DESCRIPTION OF PREFERRED EMBODIMENTS

As examples of the diseases which the composition according to the invention is useful to prevent or alleviate, there are mentioned damage of different parts of the eye such as retina tissue and lens, bronchitis, arthritis, cell proliferative changes, high blood pressure, cardiovascular diseases, age diabetes, damage to cell membranes, damage to placenta, damage to central nervous system, damage to testicles, damage to prostate or to the conduction system of the heart, emphysema, lung fibrosis, migraine headache, menstruation disorders, endothelium damage, kidney damage, multiplesclerosis, autoimmune diseases, allergies, thrombosis, and increased platelet aggreability or inhibition of prostacycline production. No allegation is intended that the present invention will prevent or alleviate all forms of the above-identified conditions, but it will prevent or alleviate those forms of the aforementioned conditions which are caused or aggravated by the presence of cadmium, aluminium or free radicals in the body.

For production of the isomer or isomers of $IP_3$ which accomplish the above objectives and which is present in the composition according to the invention, one or more of the compounds $IP_6$, $IP_5$ or $IP_4$ or a natural product containing at least one of these compounds can be used as a starting material. In the cases where the starting material is a natural product, one with a content of at least 0.3%, preferably at least 1% of inositol phosphate ($IP_6+IP_5+IP_4$) is preferably chosen. Particularly suitable products are beans, bran, pollen and seeds of oil plants.

The composition according to the present invention should preferably contain at least 10%, preferably at least 20%, or better yet at least 40% $IP_3$ calculated on the inositol content of the starting material. As high a level as possible of $IP_3$ in the composition is aimed at, as $IP_3$ has the best therapeutic effect according to experiments shown below. The $IP_3$ isomers present in the composition according to the invention can, for example, be produced by enzymatic breakdown starting form $IP_4$, $IP_5$ and/or $IP_6$.

According to the invention a procedure where the above mentioned higher inositol phosphates $IP_6$, $IP_5$ and/or $IP_4$ are broken down enzymatically to $IP_3$ with phytase enzyme, for instance, is preferred. Phytase enzyme is normally present in all inositol phosphate containing plants and seeds. Because of this it is, according to the invention, usually not necessary to add the enzyme if a natural product is used as starting material. In the cases where the natural product has too low an enzymatic activity or when $IP_6$, $IP_5$ or $IP_4$ or a mixture of these is used as starting material, a phytase enzyme, for example, from bran is added.

A suitable way to treat the natural or crude starting material is to pretreat it, for instance by breakage or removal of outer membrane and removal of unwanted constituents. Thus, when using pollen the allergens should be removed. Thereafter the material is soaked in water to make the inositol phosphate available for breaking down and to activate the enzyme. In the cases where an extra quantity of enzymes is necessary, this quantity is added at this stage. The enzyme is then allowed to act for so long a time as is necessary for the intended degree of hydrolysis to be achieved.

The hydrolysis takes place at a suitable temperature, usually 20°–70° C., preferably 30°–60° C. and at optimal pH-level for the phytase present. In order to stop the hydrolysis at the intended level the enzyme may be destroyed or inactivated, for instance by a rapid heating of the hydrolysed starting material. This also ensures that an uncontrolled and undesired continued hydrolysis of $IP_3$ in the stomach will not continue when the composition is administered. In order to transfer the material to a form which is stable at storage it can suitable be freeze dried. Yeast can be used advantageously as a source of phytase. Preferably baker's yeast is used. When using yeast essentially only one isomer of $IP_3$ is obtained, namely D-myo-inositol-1.2.6-triphosphate.

The above mentioned procedure, in applicable parts with possible modifications, can be used also when one or more of the compounds $IP_6$, $IP_5$ or $IP_4$ per se are used as starting material.

The pharmaceutical composition according to the invention comprises as a pharmaceutically active ingredient at least one isomer of inositol triphosphate ($IP_3$) in an amount sufficient to reduce the negative effect of cadmium or aluminium in the body or inhibit or reduce the formation of free radicals in the body.

It is suitable that the composition according to the invention exists in unit dosage form. Tablets, granulates or capsules are suitable administration forms for such unit dosage. Furthermore, tablet and granulates can easily be surface treated such as to provide an enteric coating to prevent an uncontrolled hydrolysis in the stomach and to bring about a desired absorption in the intestine. Other suitable administration forms are slow release and transdermal administration. A usual pharmaceutically acceptable additive, excipient and/or carrier can be included in the composition. The tablets or granulates can also contain a disintegrant which causes the tablets or the granulates, respectively, to disintegrate easily in the intestine. In certain cases, especially in acute situations, it is preferable to use the unit dosage in the form of a solution for intravenous administration.

The pharmaceutical composition can also consist as such of $IP_3$ solely without any additive, expedient or carrier.

If desired, the composition can be free of other inositol phosphates, $IP_1$, $IP_2$, $IP_4$, $IP_5$ and $IP_6$. Accordingly, the mixture of $IP_3$ isomers can have a purity of 90–100%, such as 93–100% or preferably 95–100%.

Alternatively, the pharmaceutical composition can consist of or comprise one or more specific $IP_3$ isomers disclosed hereinafter, each present in substantially pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

The production of $IP_3$ and the isolation of the different isomers thereof are disclosed in the above mentioned co-pending application (applicant's file No. 355 b).

It is in most cases suitable that the $IP_3$-isomer or isomers in the composition according to the invention be present in salt form in order not to affect the mineral balance negatively. The salt should preferably consist of a sodium, calcium, zinc, copper or magnesium salt or a mixture of two or more of these salts. Calcium and zinc salts or mixtures of these are especially preferred as calcium and zinc ions can compete with cadmium ions at binding to vital sites in the body. In this way the resorption and negative effects of cadmium in the body are further decreased and a preventive and therapeutic effect on the above diseases is reached. The isomer of $IP_3$ can also partly be present as a salt of one or more physiologically acceptable compounds in the lanthanide series; i.e. La, Ce, Pr, Nd, Pm, Sm, Eu, Gd, Tb, Dy, Ho, Er, Tm, Yb and Lu.

For the above mentioned reasons it is also an advantage if the composition contains a surplus or an extra addition of at least one pharmaceutically acceptable salt of calcium, zinc, magnesium or copper with a mineral acid or organic acid. This is especially valuable for older persons who are often deficient in these minerals.

The composition according to the present invention can preferably also contain at least one substance containing selenium, an unsaturated fatty acid, such as gamma linoleic acid, vitamin E, vitamin C or a pharmaceutically acceptable organic acid or salt thereof, such as citrate, oxalate, malonate and tartrate. These substances also help to counteract the negative effect of cadmium in the body and/or give in addition thereto, in certain cases, a desirable effect together with the $IP_3$ isomer in the composition. The content of selenium in the composition is preferably such that the daily intake is about 0.7–8 µg/kg body weight preferably 0.7–3.3 µg. For vitamin E the corresponding values are about 0.1–2 mg and 0.1–1 mg, respectively.

The composition is suitably free from penicillin.

For administration to human patients suffering from a condition caused or aggravated by the presence of cadmium, aluminum or free radicals in the body, appropriate dosages can routinely be determined by those skilled in this art by extension of the results obtained in animals at various dosages. The preferred dosage for humans falls within the range of 0.1 to 10 mg $IP_3$/day/kg body weight.

In animal experiments, no toxic effects were seen after administration of very high doses of $IP_3$, 160 mg/kg body weight by intravenous injection to mice or 1600 mg/kg body weight by intraperitoneal injection to mice.

The composition according to the present invention contains at least one, sometimes two or more of the following substances which correspond to the essential $IP_3$-isomer or isomers mentioned above:

D-myo-inositol-1.2.6-triphosphate of the formula

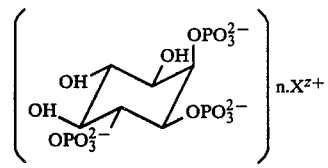

where X is hydrogen, at least one univalent, divalent or multivalent cation, or a mixture thereof, n is the number of ions, and z is the charge of the respectively ion;

D-myo-inositol-1.2.5-triphosphate of the formula

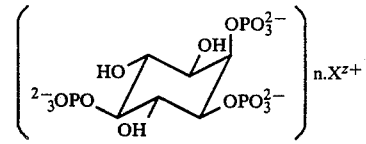

where X, n and z have the above mentioned meaning;

myo-inositol-1.2.3-triphosphate of the formula

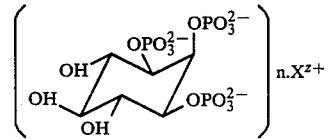

where X, n and z have the above mentioned meaning;

L-myo-inositol-1.3.4-triphosphate of the formula

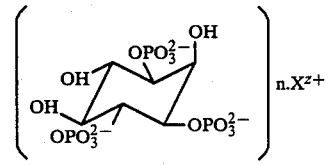

where X, n and z have the above mentioned meaning; and

D-myo-inositol-1.4.5-triphosphate of the formula

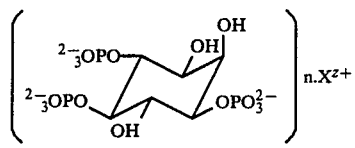

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of above isomers D-myo-inositol-1.2.6-triphosphate is preferred.

$IP_3$ may be the sole pharmaceutically active ingredient in the composition. However, also other pharmaceutically active ingredients can be present therein. The amount of $IP_3$ should then constitute 5 to 95 or 15 to 80, such as 25 to 60 percent by weight of said active ingredients.

Moreover, the composition can be a multi-vitamin unit containing 2 to 60, such as 2 to 40 or preferably 2 to 25 percent by weight of $IP_3$ based on the total weight of pharmaceutically active ingredients.

The composition usually contains 0.01-1.5 g, such as 0.05-1.3 or preferably 0.1-1 g of $IP_3$.

The present invention also relates to a method of reducing the negative effect of cadmium or aluminum ion or free radicals in the body tissues. Said method comprises administering to a person or an animal, i.e. mammals an amount of inositol triphosphate to interfere with cadmium or aluminum ion or inhibit or reduce the formation of free radicals in the body.

The invention also comprises a method of preventing or alleviating one of the following conditions; an arthritic condition, bronchitis, a cell proliferation change, high blood pressure, a cardiovascular disease, age diabetes, damage to the placenta, damage to the testicles, damage of different parts of the eye such as retina tissue and lens, damage to the prostate, damage to cell membranes, damage to the central nervous system, damage to the conducting system of the heart, emhpysema, lung fibrosis, migraine headache, menstruation disorders, endothelium damage, kidney damage, an allergy, thrombosis, multiple sclerosis, increased platelet aggregation or inhibition of the prostacycline production and wherein said condition is attributably to or is caused or aggravated by the presence of cadmium or free radicals in the body.

The method comprises administering to a human or an animal an amount of inositol triphosphate sufficient to obtain said prevention or alleviation.

Furthermore, the invention covers a method of alleviating the detrimental effect of radiation in the body, which method comprises administering to a human or an animal an amount of inositol triphosphate sufficient to alleviate said effect of radiation. For instance the radiation can be X-ray or nuclear radiation, but other kinds of radiation are also contemplated.

The invention is further explained below in connection with embodiment examples, of which example 1 shows the occurence of platelet aggregation in blood samples of rabbits after injection with cadmium. Examples 2-5 show that such aggregation can be counteracted by injection or oral administration of $IP_3$. Example 6 illustrates the occurrence of cadmium in different organs of mice after injection with cadmium. Example 7 shows the effect of $IP_2$, $IP_3$ and $IP_4$ respectively on the cadmium content in different organs of mice which had got an injection of cadmium. As disclosed in example 8, D-myo-inositol-1.2.6-triphosphate gave a strong decrease of cadmium concentration in lung, aortic artery, heart and spleen of mice which had got an injection of cadmium. Example 9 shows that $IP_3$ prevents an increase of platelet aggregation in humans caused by smoking. In example 10 it is shown that an increased blood glucose level in mice caused by free radicals can be counteracted by injection of $IP_3$. Examples 11-25 show that $IP_3$ prevents or reduces the formation of free radicals, Examples 16-17 illustrate experiments on binding constants for zinc and cadmium to $IP_6$ and $IP_3$ respectively. Examples 18-24 show production of $IP_3$ and the separation thereof into different isomers. Example 25 shows the production of a solution of a calciumsalt of D-myo-inositol-1.2.6-triphosphate for injection. In example 26 the production of tablets of the calciumsalt of D-myo-inositol-1.2.6-triphosphate is disclosed.

METHODS FOR EXAMPLES 1-5

Rabbits (New Zealand white, males) weighing 2-2.5 kg were used. They were fed a diet free from inositol phosphates, for 10 days before the experiment.

Animal experimental procedure:

In Examples 1-3 (intravenous injection of test-substances), the following procedure was used:

| Time: | Treatment |
|---|---|
| 0 minutes: | Intravenous injection of inositol phosphate in 1 ml physiological saline, or 1 ml physiological saline respectively. |
| 1 minute: | Blood sample 1 (9 ml + 1 ml 3.8% sodium citrate) taken. |
| 2 minutes: | Intravenous injection of 4 microgram Cd as $CdCl_2$ in 0.5 ml physiological saline, or 0.5 ml physiological saline respectively. |
| 5 minutes: | Blood sample 2 (9 ml + 1 ml 3.8% sodium citrate) taken. |

In Examples 4-5 (oral administration of test substances) the same procedure was used except that the first injection was replaced by oral administration of the inositol phosphates or saline respectively. Injection volumes were the same as those above. The oral dosing was made 1 hour before blood sample 1. The blood sampling and the second intravenous injection were made as above. The rabbits were unanesthetized during the experiments.

Treatment of samples

The two blood samples from each animal were centrifuged at 1200 revolutions per minute, for 10 minutes, and the plasma with platelets was obtained.

The plasma with platelets from the two samples was analyzed concerning the response to addition of ADP (adenosin diphosphate) in an aggregometer (Chronopar Corp Mod, 440) according to Born (J. Physiol: 67,1968). The two samples were analyzed simultaneously at the same concentration (1-20 micromolar) of ADP, in the two channels of the instrument.

The principle of this test is that the plasma with platelets is turbid, and has a low transmittance for light. As ADP is added, the platelets aggregate, and form clumps. This results in an increase of transmittance which is quantified by the instrument. The response to ADP was measured in scale units, with 80 scale units representing maximal aggregation. In order to have a maximal sensitivity of the method to pick up changes in platelet reactivity, the ADP dose should cause a response of 5-30 scale units. This was normally achieved with 5 μM ADP, but in some animals a lower or higher dose (1-20 μM) was necessary.

The results of the test is expressed as maximal aggregation in sample 2 (scale units) minus maximal aggregation in sample 1. In example 1, mean values of aggregation in the two samples is also given.

An increase in platelet aggregation has been reported to occur after smoking, and in cardiovascular diseases, and agents which suppress platelet aggregation are believed to be of value in treating, for example, cardiovascular diseases.

EXAMPLE 1

Methods were as described above. Injection 1 was always saline, and injection 2 was saline (13 animals) or Cd (14 animals).

The results were:

|  | Aggregation Sample 1 (scale units) | Aggregation Sample 2 (scale units) | Change from Sample 1 to sample 2 (scale units) |
|---|---|---|---|
| Saline-treated | 18.2 | 17.1 | −1.1 |
| Cd-treated | 21.4 | 24.8 | +3.4 |

Thus, Cd-treatment caused an increase in platelet aggregation, while a slight decrease was seen in the saline-treated animals.

EXAMPLE 2

Methods were as described above. The rabbits were intravenously injected with $2.10^{-6}$ mol inositoldiphosphate ($IP_2$), inositoltriphosphate ($IP_3$) or inositoltetraphosphate ($IP_4$) dissolved in physiological saline. The inositol phosphate $IP_2$, $IP_3$ or $IP_4$ respectively consisted of mixtures of the isomers which are formed when $IP_6$ is hydrolysed with wheat phytase.

The following results were obtained. The Cd-treated rabbits from Example 1 are included for comparison:

| Injection 1 | Injection 2 | Number of animals | Change in platelet aggregation from sample 1 to sample 2 (scale units) |
|---|---|---|---|
| $IP_2$ | Cd | 9 | +1.9 |
| $IP_3$ | Cd | 8 | −0.2 |
| $IP_4$ | Cd | 9 | +5.6 |
| Saline | Cd | 14 | +3.4 |

The results show that $IP_3$ prevented the aggregating effect of cadmium. $IP_2$ had a weak preventive effect while $IP_4$-treated animals showed even more aggregation.

EXAMPLE 3

Methods were as above. Four different isomers of $IP_3$ were tested, the injected amount was $2\times10^{-7}$ mol. The isomers were D-myo-inositol-1.2.6-triphosphate (1.2.6), L-myo-inositol-1.3.4-triphosphate (1.3.4), myo-inositol-1.2.3-triphosphate (1.2.3) and D-myo-inositol-1.2.5.-triphosphate (1.2.5).

The results were as follows: (Cd-treated animals from example 1 are included for comparison).

| Injection 1 | Injection 2 | No | Change in aggregation from sample 1 to sample 2 (scale units) |
|---|---|---|---|
| 1.2.6 | Cd | 15 | −0.4 |
| 1.2.3 | Cd | 12 | +0.3 |
| 1.3.4 | Cd | 13 | +0.6 |
| 1.2.5 | Cd | 14 | +1.7 |
| Saline | Cd | 14 | +3.4 |

The results show that all the tested isomers had a good effect in preventing the cadmium-induced aggregation, and that the best effect was obtained with 1.2.6.

EXAMPLE 4

The methods were as above. $IP_3$ (D-myo-inositol-1.2.6-triphosphate), dose $2\times10^{-6}$ mol in 1 ml physiological saline or saline only was given orally.

The results were as follows:

| Oral administration | Injection | No | Change in aggregation from sample 1 to sample 2 (scale units) |
|---|---|---|---|
| Saline | Cd | 23 | +1.9 |
| $IP_3$ | Cd | 20 | +1.1 |

As in Example 1, Cd caused an increase in platelet aggregation. At this dose, $IP_3$ given orally partly prevented this increase.

EXAMPLE 5

The methods were as above. $IP_3$ (D-myo-inositol-1.2.6-triphosphate), dose $2\times10^{-5}$ mol, was given orally. The saline +Cd-treated animals from Example 4 are included for comparison.

The following results were obtained:

| Oral administration | Injection | No | Change in aggregation from sample 1 to sample 2 |
|---|---|---|---|
| Saline | Cd | 23 | +1.9 |
| $IP_3$ | Cd | 15 | −0.4 |

At the dose used in this experiment, $IP_3$ prevented the effect of Cd on platelet aggregation.

An increase in platelet aggregation is regarded as one of the most important factors causing arteriosclerosis, and the ability of $IP_3$ to prevent the aggregation induced by cadmium (Examples 2-5) and smoking (Example 9) shows that $IP_3$ is very useful in preventing or alleviation such disease.

EXAMPLE 6

14 mice were kept on a diet free of phytic acid and inositol phosphates for 1 week before the experiment and through the experiment. The mice were injected intravenously with 2.5 microcurie $^{109}Cd$ as $CdCl_2$ dissolved in 50 microliters of physiological saline. 7 days after the injection, the mice were killed, several organs were dissected out and weighed. The level of radioactive cadmium in the organs was determined by counting in a gammacounter. Results were as follows:

| Organ | Counts/minute/mg tissue |
|---|---|
| Liver | 542.3 |
| Kidney | 356.3 |

-continued

| Organ | Counts/minute/mg tissue |
|---|---|
| Heart | 53.5 |
| Aortic wall | 29.4 |
| Lung | 31.5 |
| Muscle | 7.3 |
| Fat | 1.8 |

Compared with general body tissues such as muscle or fat tissue, significant amounts of Cd accumulated in organs (heart, aortic wall, lung) where Cd-induced diseases have been found in experimental animals.

The high level of Cd in the liver and kidney is explained by the fact that these tissues contain metallothionein which binds and detoxifies cadmium. Thus, although these organs take up most of the Cd, no damage will occur until very high levels are reached.

EXAMPLE 7

Mice weighing 18-20 gram at the start of the experiment were used. During the experiment and for at least seven days before the experiment the mice were fed a semisynthetic diet free of inositol phosphates. The mice were divided in four groups.

They received daily intraperitoneal injections of physiological saline, inositol diphosphate ($IP_2$), inositol triphosphate ($IP_3$) or inositol tetraphosphate ($IP_4$) for 9 days. The dose of inositol phosphates was $10^{-8}$ mol/day. The injected volume was 0.2 ml. $IP_2$, $IP_3$ and $IP_4$ were mixtures of the isomers which are formed when phytic acid is degraded by wheat phytase.

On day two of the experiment, 5-10 minutes after the second intraperitonial injection, all mice received an intravenous injection of 2.5 microcurie of $^{109}Cd$ as cadmium chloride in 50 ul of saline. After the last intraperitonial injection the mice were killed and several organs were dissected out and weighed.

Radioactivity in the different organs were measured by counting with a gamma-counter. Radioactivity in the organs of the $IP_3$-treated animals was compared with that of control animals which had been treated with saline for the same period of time. In the results radioactivity in the organs of the animals treated with the different inositol phosphates is expressed as % of the radioactivity found in controls. The results were as follows:

Organ levels of Cadmium mice treated with $IP_2$, $IP_3$, $IP_4$ as percent of control levels (controls=100). 15 mice in each group.

| Organ | $IP_2$ | $IP_3$ | $IP_4$ |
|---|---|---|---|
| Lung | 111 | 80 | 113 |
| Heart | 99 | 77 | 89 |
| Aorta | 95 | 89 | 81 |
| Spleen | 151 | 81 | 132 |
| Salivary gland | 104 | 82 | 89 |
| Liver | 100 | 100 | 101 |
| Kidney | 101 | 102 | 94 |

The results show that $IP_3$ caused a reduction in cadmium levels in all studied organs except liver and kidney. With $IP_4$, a reduction in some, but not all organs was seen, and no positive effect was seen with $IP_2$.

EXAMPLE 8

The experiment in Example 7 was repeated with the difference that the pure isomer D-myo-inositol-1.2.6-triphosphate was used. The dose was $10^{-6}$ mole per day and the mice received 4 daily injections. A control group received saline injections. The results were as follows:

Organ levels of cadmium in mice treated with D-myo-inositol-1.2.6-triphosphate, expressed as percent of control values.

| Organ | Cd-level |
|---|---|
| Lung | 74 |
| Heart | 67 |
| Aorta | 65 |
| Spleen | 57 |
| Salivary gland | 87 |
| Liver | 100 |
| Kidney | 104 |

These results show that the 1.2.6 isomer of $IP_3$ causes a strong decrease in cadmium concentration in lung, aortic artery, heart and spleen. Liver and kidney levels were not affected.

EXAMPLE 9

The effect of $IP_3$ on platelet aggregation after smoking in humans was studied.

Four young healthy male non-smokers recieved, on two occasions, a capsule containing 50 mg of $IP_3$ or 50 mg of a placebo. The $IP_3$ used was the Ca-salt of D-myo-inositol-1.2.6-triphosphate. Neither subject nor investigator knew whether the subject had received $IP_3$ or placebo.

Two hours after ingestion of the capsule, a blood sample was obtained. The subject then smoked two cigaretts in rapid succession. A second blood sample was obtained after smoking. The aggregation responses of the platelets to ADP and collagen in the two samples were determined, using essentially the same procedure as in Example 1. The results are expressed as change in aggregation from the pre-smoking to the post-smoking sample. A positive sign indicates that aggregation was stronger after smoking.

| Aggregating agent | Concentration of aggregating agent | | $IP_3$ | Placebo | Difference between $IP_3$ and placebo |
|---|---|---|---|---|---|
| ADP | 0.5 | mmol | +1.5 | +7.25 | 5.85 |
| " | 1 | mmol | −1.5 | +0.25 | 1.75 |
| " | 2.5 | mmol | −1.5 | 0 | 1.5 |
| " | 5 | mmol | −2.5 | −0.75 | 1.75 |
| Collagen | 0.5 | mg | +5.15 | +12.25 | 6.5 |
| " | 1 | mg | −8.25 | +1.75 | 10.0 |
| " | 2.5 | mg | −3.75 | 0 | 3.75 |
| " | 5 | mg | −1.5 | −0.25 | 1.25 |

In the placebo group, smoking caused an increase in aggregation, which was most marked at low concentrations of aggregation agents. In all cases this effect was counteracted by $IP_3$. Thus $IP_3$ prevents increase of platelet aggregation caused by smoking.

EXAMPLE 10

Mice, 10 in each group, were injected intraperitoneally with $IP_3$ (Na-salt of D-myo-inositol-1.2.6-triphosphate) in three dose levels or with physiological saline. 30 minutes after this injection, all mice except one control group received an intravenous injection of alloxan, 50 mg/kg in saline.

The animals were starved for 12 hours before, and one hour after the alloxan injection. 72 hours after the alloxan injection, a blood sample from the mice were analyzed with respect to glucose level. The results were as follows:

| Dose of IP$_3$ mg/kg | Dose of alloxan mg/kg | Blood glucose |
|---|---|---|
| 0 | 0 | 216 |
| 0 | 50 | 864 |
| 800 | 50 | 857 |
| 1600 | 50 | 677 |

Alloxan causes diabetes and increased blood glucose level by promotion free radical reactions in the insulin producing cells. With IP$_3$ there was a dose-dependent decrease in blood glucose levels, and the highest dose gave some protection to the alloxan.

EXAMPLE 11

An aqueous solution containing 0.3 mM FeCl$_3$, 5.0 mM ethylenediaminotetraacetic acid (EDTA), 50 mM tris (hydroxymethyl)-aminomethan (TRIS) and 1.0 M NaN$_3$ was prepared. In the solution the complex Fe$^{3+}$-EDTA-N$_3$ was formed.

A maximum in absorption of light was detected at the wavelength of 409 nm.

Another aquaeous solution containing 0.3 mM FeCl$_3$, 50 mM EDTA and 50 mM TRIS was prepared. In the solution the complex Fe$^{3+}$-EDTA-H$_2$O was formed. There was no maximum in absorption of light detected at the wavelenght of 409 nm.

The above difference in result depends on that N$_3^-$ competitively replaces one water molecule which binds to the Fe$^{3+}$-EDTA-complex. This in turn shows that the Fe$^{3+}$-EDTA-complex has a binding site, which is occupied by a dissociable water-molecule.

It is further known that iron catalyses the formation of hydroxylradicals. For the formation of these the binding of one water molecule to iron is required.

This means that EDTA in the EDTA-Fe$^{3+}$-complex can not inhibit the formation of hydroxyl radicals catalysed by iron.

The above experiment was repeated with the difference that the EDTA was substituted with IP$_3$.

No maximum in absorption was obtained at the wavelength 409 nm.

This result means that the Fe$^{3+}$-complex with IP$_3$ does not bind water. Therefore the formation of free radicals is prevented.

EXAMPLE 12

A reaction mixture consisting of 48 mmol KH$_2$PO$_4$, 2 mmol Na-ascorbate, 0.1 mmol H$_2$O$_2$, 0.5 mmol Fe and 1.7 mmol deoxyribose was incubated at 37° C. for 1 hour. Similar reactions mixtures including EDTA 1 mmol or inositoltri-phosphate (IP$_3$) 1 mmol was similarly incubated. The IP$_3$ used was D-myo-inositol-1.2.6-triphosphate.

After incubation 1.65 ml thiobarbituric acid in 50 mmol NaOH and 1.65 ml 2.8% trichloroacetic acid was added to 2 ml of the reaction mixture. The mixture was heated to 100° C. for 20 minutes and the absorbance at 532 nm was measured with water as a blank.

The experiments were performed with iron in the form of Fe$^{2+}$(Fe(NH$_4$)SO$_4$) and Fe$^{3+}$(Fe Cl$_3$). The results were as follows:

Production of free radicals catalyzed by Fe$^{2+}$ and Fe$^{3+}$ in the presence of IP$_3$ or EDTA, expressed as absorbance at 532 nm.

| Group | Fe$^{2+}$ | Fe$^{3+}$ |
|---|---|---|
| Control | 0.76 | 0.79 |
| EDTA | 2.2 | 1.86 |
| IP$_3$ | 0.46 | 0.43 |

These results show that the formation of free radicals in the reaction mixture was diminished by 40% after addition of IP$_3$. The addition of EDTA had an opposite effect. It strongly increased production of free radicals. Thus IP$_3$ was shown to reduce iron-dependent formation of free radicals.

EXAMPLE 13

Lipid peroxidation was studied in lipid micelles. The following reaction mixture was incubated for 2 hours at 37° C.:

| | |
|---|---|
| 0.4 ml | Clark-Lubs buffer pH 5.5 |
| 0.2 ml | phospholipid liposomes |
| 0.1 ml | IP$_3$ 0.5–5 mM or 0.1 ml H$_2$O |
| 0.1 ml | Fe$^{2+}$ 1 mM or 0.1 ml H$_2$O |
| 0.1 ml | Al$^{3+}$ 4 mM or 0.1 ml H$_2$O |
| 0.1 ml | H$_2$O |

The IP$_3$ was d-myo-inositol-1.2.6-triphosphate. After incubation, 0.5 ml of Thiobarbituric acid + 0.5 ml 25% HCl was added and the mixture was heated at 100° C. for 15 minutes. 1 ml lubrol PX 1% (Sigma) wwas added and lipid peroxidation was measured by measuring absorbance at 532 nm. The results were as follows:

| | Concentration, mM | | | Absorbance |
|---|---|---|---|---|
| Experiment | Fe$^{2+}$ | Al$^{3+}$ | IP$_3$ | 532 nm |
| 1 | 0.1 | 0 | 0 | 0.36 |
| 2 | 0 | 0.4 | 0 | 0.12 |
| 3 | 0.1 | 0.4 | 0 | 0.89 |
| 4 | 0.1 | 0.4 | 0.5 | 0.36 |
| 5 | 0.1 | 0 | 0.5 | 0.30 |
| 6 | 0.1 | 0 | 0.4 | 0.26 |
| 7 | 0.1 | 0 | 0.2 | 0.29 |
| 8 | 0.1 | 0 | 0.1 | 0.28 |
| 9 | 0.1 | 0 | 0.05 | 0.27 |
| 10 | 0 | 0 | 0 | 0.13 |

Fe$^{2+}$ caused lipid peroxidation (group 1 vs 10). Al$^{3+}$ itself caused no peroxidation (2 vs 10) whereas the combination of Fe$^{2+}$+Al$^{3+}$ caused much stronger peroxidation than Fe$^{2+}$ alone (1 vs 3). Addition of IP$_3$ completely prevented the interaction between Fe$^{2+}$ and Al$^{3+}$ (3 vs 4). In systems with only Fe$^{2+}$, IP$_3$ caused marked reduction in radical formation (1 vs 5–9).

EXAMPLE 14

Lipid peroxidation was studied in lipid micelles. The following reaction mixture was incubated for 2 hours at 37° C.:

| | |
|---|---|
| 0.4 ml | Clark-Lubs buffer pH 5.5 |
| 0.2 ml | phospholipid liposomes |
| 0.1 ml | IP$_3$ 10 mM or 0.1 ml H$_2$O |
| 0.1 ml | Fe$^{2+}$ 1 mM |
| 0.1 ml | Cd$^{2+}$ 1 mM or 1 ml Pb$^{2+}$ 1 mM or 0.1 ml H$_2$O |

-continued

| 0.1 ml | H₂O |
|---|---|

The IP₃ was D-myo-inositol-1.2.6-triphosphate. After incubation, 0.5 ml of Thiobarbituric acid +0.5 ml 25% HCl was added and the mixture was heated at 100° C. for 15 minutes. 1 ml lubrol PX 1% (Sigma) was added and lipid peroxidation was measured by measuring absorbance at 532 nm. The results were as follows:

| Experiment | Concentration, mM | | | Absorbance 532 nm |
|---|---|---|---|---|
| | $Cd^{2+}$ | $Pb^{2+}$ | IP₃ | |
| 1 | 0 | 0 | 0 | 0.63 |
| 2 | 0.1 | 0 | 0 | 1.08 |
| 3 | 0.1 | 0 | 1.0 | 0.73 |
| 4 | 0 | 0.1 | 0 | 1.79 |
| 5 | 0 | 0.1 | 1.0 | 1.32 |

The lipid peroxidation caused by $Fe^{2+}$ (group 1) was strongly increased by Cd (2) and by Pb (4). The effects of both these metals was strongly counteracted by IP₃ (3 vs 2 and 5 vs 4).

EXAMPLE 15

Reaction mixtures with the following compositions were incubated for 5 minutes at 37° C.:

| KH₂PO₄ buffer pH 7.4 | 20 mM |
|---|---|
| EDTA | 0.1 mM |
| Salicylate | 1 mM |
| Ascorbate | 1 mM |
| H₂O₂ | 3.3 mM |
| $Fe^{3+}$ | 0.05 mM |
| IP₃ | 0, 2.5, 5 or 10 mM |

The products formed by oxidation of salicylate were quantified with HPLC. The IP₃ was d-myo-inositol-1.2.6-triphosphate.

The system studies radical scavenging. Under these reaction conditions, all $Fe^{3+}$ will form complex with EDTA. The Fe-EDTA complex will induce free radical formation, and the ability of IP₃ to prevent oxidation of salicylate is studied.

The results of the experiment were:

| Concentration of IP₃, mM | Relative amount of salicylate oxidized |
|---|---|
| 0 | 100 |
| 2.5 | 44 |
| 5 | 43 |
| 10 | 19 |

Thus, IP₃ is able to act as a radical scavenger, thereby preventing free radical induced damage to other molecules.

EXAMPLE 16

5 ml of an aqueous solution containing 2 umol IP₆ and an equivalent amount of cations was titrated with 10 mM sodium hydroxide solution.

The cations were cadmium- and zincions in the form of cadmium chloride and zinc sulphate.

pH was determined as the function of the amount added sodium hydroxide.

The experiment above was repeated with IP₃.

The result of the experiments was that in the pH-range 4–8 zinc binds stronger than Cd to IP₆. For IP₃ the reverse is true, ie cadmium binds stronger than zinc.

EXAMPLE 17

The binding constant for the complex IP₃-cadmium was estimated with NMR.

The constant were estimated through comparative studies of other complexes like EDTA-cadmium and parvalbumine-cadmium.

The binding constant (K) for IP₃-cadmium was $10^9$.

EXAMPLE 18

Hydrolysis of sodium phytate with wheat phytase and fractionation of a mixture of inositolphosphates.

A 1.6 gram quantity of sodium phytate (from corn, Sigma Chemical Co) was dissolved in 650 ml sodium acetate buffer, pH 5.2. 2.7 gram wheat phytase (EC 3.1.3.26, 0.015 U/mg, from Sigma Chemical Co) was added and the mixture was incubated at 38° C.

The dephosphorylation was followed by determining the inorganic phosphorus released. After 3 hours when 50% inorganic phosphorus was liberated the hydrolysis was stopped by adding 30 ml ammonia to pH 12. A liquid mixture containing inositolphosphates was obtained.

350 ml of the mixture was passed through an ion-exchange column (Dowex 1, chloride form, 25 mm×250 mm) and eluted with a linear gradient of hydrochloric acid (0–0.7N HCl). Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphate etc. Two fractions with the ratio of phosphorus to inositol of three to one were obtained.

EXAMPLE 19

Fractionation of inositoltriphosphates 100 ml of the first fraction obtained in Example 18 with a phosphorus/inositol ratio of three to one was neutralized and precipitated as a bariumsalt after addition of 10% excess of 0.1M bariumacetate solution. 600 mg of the precipitated salt was dissolved in 50 ml 0.18N hydrochloric acid. The solution was separated on an ion-exchange column (Dowex 1, chloride form, 25 mm×2500 mm) with diluted hydrochloric acid as eluent. Aliquots of eluted fractions were analyzed for phosphorus. Three peaks consisting of isomers of inositoltriphosphates can be seen.

EXAMPLE 20

Structural determination of isomers of inositol-triphosphates with NMR.

The three peaks obtained in Example 19 were analyzed by H-NMR. Data show that the peaks consist of myo-inositol-1.2.6-triphosphate, myo-inositol-1.2.3-triphosphate and myo-inositol-1.3.4-triphosphate respectively.

The second fraction obtained in Example 18 with a phosphorus/inositol ratio of three to one was analyzed by H-NMR. Data show that the fraction consists of myo-inositol-1.2.5-triphosphate.

EXAMPLE 21

Determination of optical isomers of inositol-triphosphates.

20 mg of the compounds determined with NMR according to Example 20 to be myo-inositol-1.2.6-triphosphate and myo-inositol-1.3.4-triphosphate were further chromatographed on a chiral column based on acetylated cellulose (20 mm×300 mm from Merck) with a mixture of ethanol and water as eluent. The fractions were analyzed with a polarimeter. As can be seen each compound consists of one optical isomer, D-myo-inositol-1.2.6-triphosphate and L-myo-inositol-1.3.4-triphosphate respectively.

EXAMPLE 22

Hydrolysis of sodium phytate with baker's yeast and fractionation of a mixture of inositolphosphates.

A 0.7 gram quantity of sodium phytate (from corn, Sigma Chemical Co) was dissolved in 600 ml sodium acetate buffer pH 4.6. 50 gram of baker's yeast from Jästbolaget, Sweden (dry substance: 28%, nitrogen content: 2%; phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatant was collected.

400 ml of the supernatant was passed through an ion-exchange column (Dowex 1, chloride form, 25 mm×250 mm) and eluted with a linear gradient of hydrochloric acid (0–0.7N HCl).

Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphates etc.

EXAMPLE 23

Structural determination of isomers of inositoltriphosphate.

The fraction obtained in Example 22 with a phosphorus/inositol ratio of three to one was neutralized and evaporated before analysis with H-NMR. Data show that the peak consists of myo-inositol-1.2.6-triphosphate.

EXAMPLE 24

Determination of optical isomers of myo-inositol-triphosphate.

The same method was used as described in Example 21 with the difference that 10 mg of the compound determined with NMR according to Example 23 was analyzed. As can be seen the compound consists of one optical isomer, D-myo-inositol-1.2.6-triphosphate.

EXAMPLE 25

Solution of potassiumsalt of D-myo-inositol-1.2.6-triphosphate for injection.

0.5 g of the potassiumsalt of IP$_3$ and 0.77 g NaCl were dissolved in 98.73 ml of water for injection to form a solution suitable for injection into a person or an animal.

EXAMPLE 26

Tablets of calciumsalt of D-myo-inositol-1.2.6-triphosphate.

Tablets of the calciumsalt of D-myo-inositol-1.2.6-triphosphate were produced in the following way. 50 g calcium-salt of D-myo-inositol-1.2.6-triphosphate, 132 g lactose and 6 g acacia were mixed. Purified water was then added to the mixture, whereupon the mixing was continued until a suitabale consistency was obtained. The mixture was sieved and dried. Then the mixture was blended with 10 g talcum and 2 g magnesium stearate. The mixture was compressed into tablets each weighing 200 mg.

For purposes of further understanding the invention, formulas are given below of the IP$_3$ isomers of the invention. Formulas are also given for IP$_6$, IP$_5$, IP$_4$ and IP$_2$.

The lower phosphate-esters of myoinositol are named depending on where the phosphoric acid groups are situated on the inositol ring, with the numbering giving as low position numbers as possible. L and D stand for clock-wise and counterclock-wise counting respectively, and are used depending on which result gives the lowest position number. The carbon atom which has an axial phosphoric acid group always has the position number 2. The structural formulae below are simplified to the acid form.

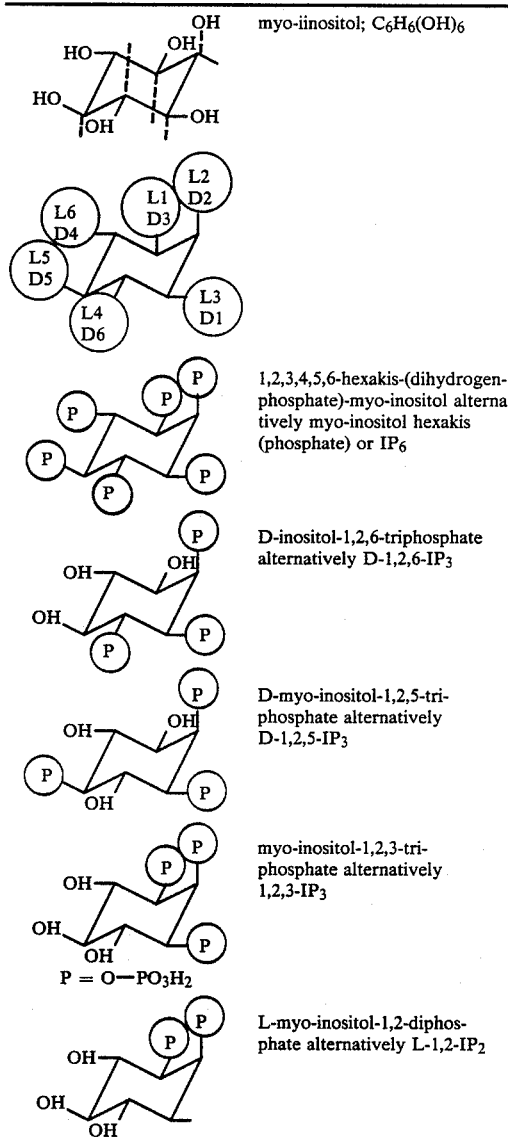

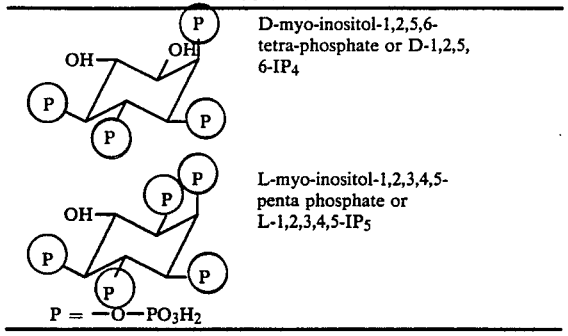

| | |
|---|---|
| | D-myo-inositol-1,2,5,6-tetra-phosphate or D-1,2,5,6-IP$_4$ |
| | L-myo-inositol-1,2,3,4,5-penta phosphate or L-1,2,3,4,5-IP$_5$ |

$P = -O-PO_3H_2$

What is claimed is:

1. A pharmaceutical composition consisting essentially of a pharmaceutically active effective amount of at least one specific isomer of inositol triphosphate (IP$_3$) and a pharmaceutically acceptable carrier, excipient or additive therefor.

2. A composition according to claim 1 wherein said inositol triphosphate is in salt form.

3. A composition according to claim 2 wheren said inositol triphosphate salt is a salt of sodium, calcium, zinc, copper or magnesium or a mixture of two or more thereof.

4. A composition according to claim 1 in tablet or granulated form.

5. A composition according to claim 1 in the form of a solution.

6. A composition according to claim 1 which further also consists essentially of a pharmaceutically acceptable salt of mineral acid or organic acid with at least one of calcium, zinc, magnesium or copper.

7. A composition according to claim 1 which further consists essentially of at least one additive selected from the group consisting of a selenium compound, vitamin E, vitamin C and a pharmaceutically acceptable organic acid or salt thereof.

8. A composition according to claim 1 wherein at least one isomer of IP$_3$ is present in substantially pure form.

9. A composition according to claim 7 wherein said salt is a citrate, oxalate, malonate or tartrate.

10. A composition according to claim 1 which is free from penicillin.

11. A composition according to claim 1 wherein said inositol triphosphate comprises D-myo-inositol-1.2.6-triphosphate with the formula

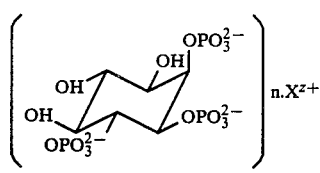

where X is hydrogen or at least one univalent, divalent or multivalent cation; n is the number of ions; and z is the charge of the respective ion.

12. A composition according to claim 11 wherein n ranges between 6 to 1 inclusive and z ranges between 1 to 6 inclusive.

13. A composition according to claim 1 wherein said inositol triphosphate comprises D-myo-inositol-1.2.5-triphosphate with the formula

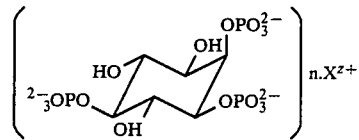

where X is hydrogen or at least one univalent, divalent or multivalent cation; n is the number of ions; and z is the charge of the respective ion.

14. A composition according to claim 1 wherein said inositol triphosphate comprises myo-inositol-1.2.3-triphosphate with the formula

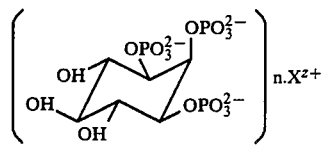

where X is hydrogen at least one univalent, divalent or multivalent cation; n is the number of ions; and z is the charge of the respective ion.

15. A composition according to claim 1 wherein said inositol triphosphate comprises L-myo-inositol-1.3.4-triphosphate with the formula

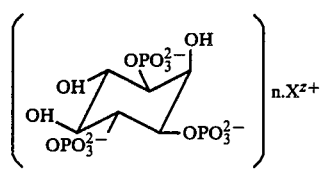

where X is hydrogen and/or at least one univalent, divalent or multivalent cation; n is the number of ions; and z is the charge of the respective ion.

16. A composition according to claim 1 wherein said inositol triphosphate comprises D-myo-inositol-1.4.5-triphosphate with the formula

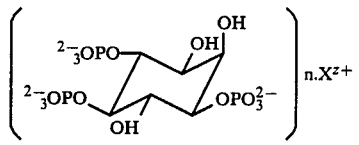

where X is hydrogen and/or at least one univalent, divalent or multivalent cation; n is the number of ions; and z is the charge of the respective ion.

17. A composition according to claim 1 wherein IP$_3$ is the sole pharmaceutically active ingredient.

18. A composition according to claim 1 containing at least one other pharmaceutically active ingredient in addition to IP$_3$.

19. A composition according to claim 18 wherein the amount of IP$_3$ is in the range of 5 to 95% by weight of the active ingredients.

20. A composition according to claim 18 which is a multivitamin unit containing 2–60% by weight of IP$_3$ based on the total weight of said pharmaceutically active ingredients.

21. A composition according to claim 1 containing 0.01–1.5 g of IP$_3$.

22. A composition according to claim 12 wherein n ranges between 3 to 6 inclusive and z is 3, 2 or 1.

* * * * *